Aug. 22, 1961 A. CHABERT ET AL Plant Pat. 2,079
ROSE PLANT
Filed Oct. 26, 1960
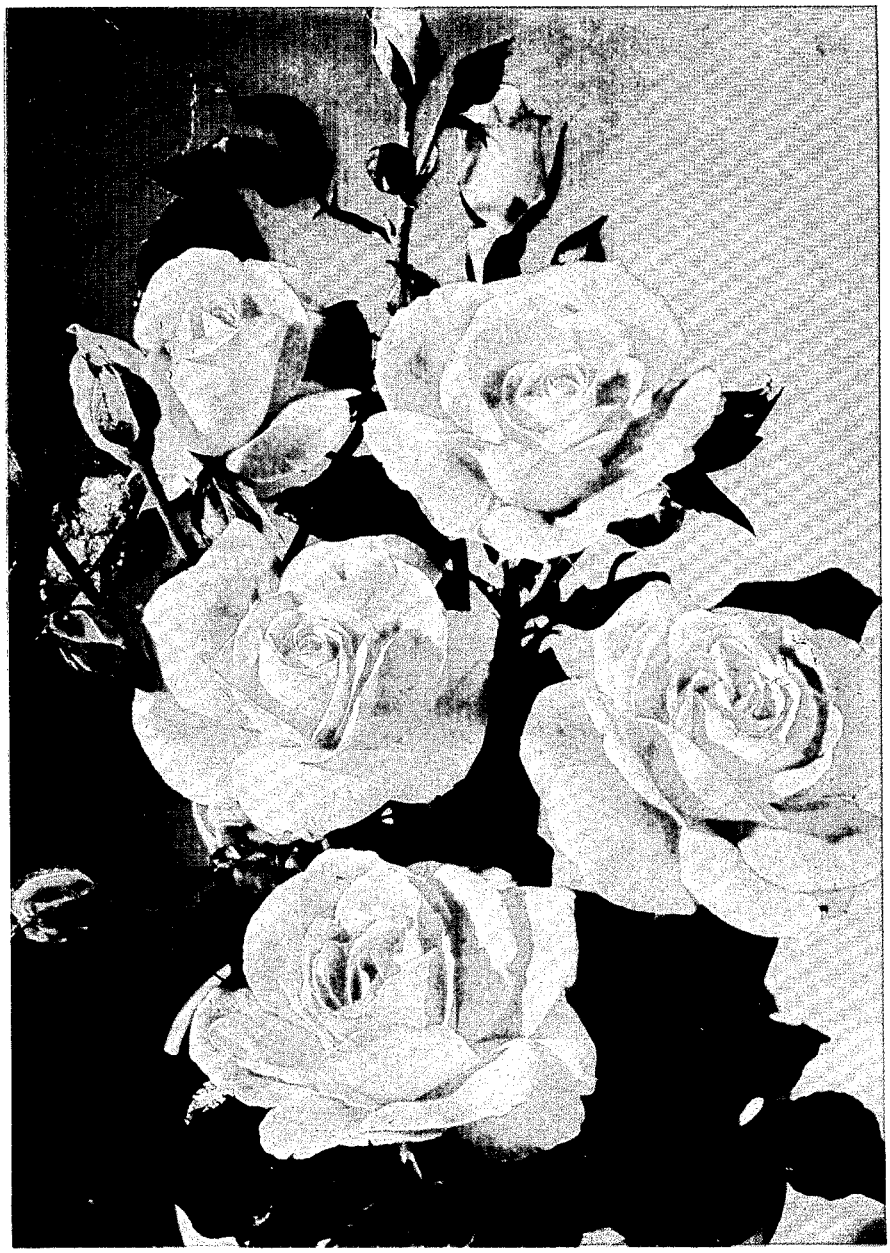
INVENTORS.
Andre Chabert
Georges Delbard
BY Robb & Robb
ATTORNEYS United States Patent Office Plant Pat. 2,079
Patented Aug. 22, 1961

2,079
ROSE PLANT

Andre Chabert and Georges Delbard, Paris, France, assignors, by mesne assignments, to Stark Bro's Nurseries & Orchards Co., Louisiana, Mo., a corporation of Missouri Filed Oct. 26, 1960, Ser. No. 65,245
1 Claim. (Cl. 47—61)

The present invention relates to a new and distinct variety of rose plant of the "grandiflora" class, which was originated by us by crossing an unnamed and unpatented seedling derived from crossing the variety "Incendie" (unpatented) × "Chic Parisien" (unpatented) with another unnamed and unpatented seedling derived from a cross of the variety "Floradora" (unpatented) × "Independence" (U.S. Plant Patent No. 1,036), said latter variety being known in Europe as "Kordes' Sondermeldung."

As the result of this breeding, we have produced a new rose variety which is endowed with unusual and desirable characteristics, particularly from a commercial standpoint, as is evident by the following unique combination of features which definitely differentiate our new variety from its antecedents, as well as from all other varieties of which we are aware:

(1) A general resemblance to the variety "Fashion" (U.S. Plant Patent No. 789) and especially to the variety "Spartan" (U.S. Plant Patent No. 1,357), but more vigorous and more resistant to disease than "Fashion," and having a very good everblooming habit, with foliage larger, more glossy and less sharply serrate than that of "Spartan";

(2) Attractive, high-centered buds that are more urn-shaped than those of "Spartan";

(3) A vigorous "floribunda" growing habit, with fewer thorns than the variety "Spartan";

(4) A habit of bearing the flowers mostly singly and on stems of good length; and (5) A distinctive, attractive and remarkably uniform Shrimp Pink-Salmon general color tonality of the flowers somewhat similar to the flower color of "Spartan," but being more nearly Mandarin Red at the base of the inner surface of the petals and shading to Vermilion at the outer edges of the petals, with consequent less bi-color appearance than that of the flowers of "Spartan."

Asexual reproduction of our new variety, as performed by us by budding in France, and also as performed on our behalf by budding at Livermore, California, U.S.A., shows that the foregoing characteristics and distinctions come true to form and are established and transmitted through succeeding propagations.

The accompanying drawings show typical specimens of the vegetative growth and flowers of our new variety in different stages of development and as depicted in color as nearly true as it is reasonably possible to make the same in a color illustration of this character.

The following is a detailed description of our new variety, with color terminology in accordance with the British Horticultural Colour Chart, except where general color terms of ordinary dictionary significance are obvious:

Type: Hardy; bush; seedling; for cut flowers and for garden decoration.
Class: "Grandiflora."
Breeding: Seedling.
*Seed parent.*—An unnamed seedling derived from a cross of "Incendie" × "Chic Parisien."
*Pollen parent.*—An unnamed seedling derived from a cross of "Floradora" × "Independence" (also known as "Kordes' Sondermeldung").

*Flower*

(Observations made from specimens grown outdoors at Livermore, California, U.S.A.)

Continuity: Continuous.
Fragrance: Slight. Nature—spicy.
Flowers borne: Singly; on good stems of medium length and normal strength.
Quantity of bloom: Abundant outdoors.
Bud:
*Peduncle.*—Long; slender; erect; almost smooth; with few red hairs and prickles. Color—light green.
*Before calyx breaks.*—Size—small. Form—short; pointed; without foliaceous appendages on the surface of the bud; with slender foliaceous much-cut parts extending beyond the tip of the bud equal to ½ of its length, with every other sepal having 2 or 3 long appendages on each side of sepal of a length up to 5/16 inch. Color.—Dutch Vermilion, Plate 717/1.
*As calyx breaks.*—Color—from Scarlet, Plate 19/1, to Delft Rose, Plate 020.
*As first petal opens.*—Size—from small to medium. Form—short; urn-shaped. Color: outside—Scarlet, Plate 19/1; inside—Mandarin Red, Plate 17/1.
*Opening.*—Opens up well both in cold and hot weather.
Bloom:
*Size (when fully open).*—From small to medium; from 3 inches to 3¼ inches.
*Petalage.*—Double; from 25–30 petals plus 5 or 6 petaloids; arranged regularly.
*Form.*—Very high-centered at first, but becoming open and showing stamens; petals at first being loosely rolled inward, but later becoming loosely rolled outward at maturity; attractive imbricated arrangement, and central petals somewhat cover stamens, thus giving a pleasing appearance to the flower.
Petals:
*Texture.*—Thin; soft; with both inside and outside satiny.
*Shape.*—Outside—ovate, with apex flat. Intermediate—ovate, with apex flat. Inside—elongate ovate, with apex flat and with one notch, but occasionally with several small notches on side.

This description of a newly opened flower was made from a rose grown outdoors in the month of August at Livermore, California, U.S.A.:

*Color.*—Outer petal: outside surface—Scarlet, Plate 19/2; inside surface—Mandarin Red, Plate 17/1, at bottom center, shading to Vermilion, Plate 18/2, at edge. Intermediate petal: outside surface—Scarlet, Plate 19/2; inside surface—Mandarin Red, Plate 17/1, at bottom center, shading to Vermilion, Plate 18/2, at edge. Inner petal: outside surface—Scarlet, Plate 19/2; inside surface—Mandarin Red, Plate 17/1, at bottom center, shading to Vermilion, Plate 18/2, at edge.

This description was made from a rose that was open for three days outdoors in the month of July at Livermore, California, U.S.A.:

*Color.*—Outer petal: outside surface—Carmine Rose, Plate 621/1; inside surface—Porcelain Rose, Plate 620. Inner petal: outside surface—Carmine Rose, Plate 621/1; inside surface—Porcelain Rose, Plate 620.
*General color effect.*—Porcelain Rose, Plate 620.
*Behavior.*—Drop off cleanly; little affected by weather conditions; retains remarkably uniform color.

*Flower longevity.*—Three days in July.

*Reproductive organs*

Stamens: Many; arranged irregularly about pistils. Color—Chinese Yellow, Plate 606/1.
Filaments: Short; most with anthers. Color—yellow.
Anthers: Medium large; open at various times. Color—yellow.
Pollen: Moderate quantity. Color—yellow.
Pistils: Many.
Styles: Very uneven; short; thin; loosely bunched. Color—Straw Yellow, Plate 604/1, heavily tinged with red anthocyanin pigment.
Stigma: Color—Straw Yellow, Plate 604/1.
Ovaries: All enclosed in calyx.
Hips: Short; globular; smooth; thin walls. Color—yellow, tinged with orange-red.
Sepals: Permanent; long; spear-shaped; recurved. Color—grey-green.
Seeds: Many.

*Plant*

Foliage:

*Leaves.*—Composed of 5–7 leaflets; normal abundance; medium large; moderately soft. round. Margin—simply serrate.

*Leaflets.*—Shape—oval, with apex acute. Base—round. Margin—simply serrate.

*Color.*—Mature: upper surface—moderately dark green; under surface—moderately light green, slightly tinged with anthocyanin. Young: upper surface—Moderately dark green; under surface—moderately light green, tinged rather heavily with anthocyanin.

*Rachis (the supporting stem of the compound leaf).*—From light to medium. Upper side—smooth. Under side—sparsely prickly, with from 3–5 small prickles.

*Stipules.*—From short to medium length; medium width; with medium long points turning out at an angle of about 45°.

*Disease resistance.*—Very resistant to mildew, as determined by comparison with other varieties grown under comparable cultural conditions at Livermore, California, U.S.A.

Growth:

*Habit.*—Dwarf; upright; much-branched.

*Growth.*—Very vigorous; attains height of from 3–3½ feet.

*Canes.*—Moderately heavy.

*Main stems.*—Color—dull green. Thorns—many; medium length; hooked downward; with long, narrow base; average size of ⅛ inch wide x ½ inch long at base, and ⅜ inch high. Prickles—none. Hairs—none.

*Branches.*—Color—dull green. Thorns—many; medium length; hooked downward; with long, narrow base; average size about 1/16 inch x 3/16 inch and ½ inch high. Prickles—none. Hairs—none.

*New shoots.*—Colors—dull green. Thorns—several; medium length; hooked downward; with long, narrow base; about ¼ inch high; color—purple anthocyanin. Prickles—none. Hairs—none.

We claim:

A new and distinct variety of rose plant of the "grandiflora" class, substantially as herein shown and described, characterized particularly as to novelty by the unique combination of a general resemblance to the variety "Fashion" (U.S. Plant Patent No. 789) and especially to the variety "Spartan" (U.S. Plant Patent No. 1357), but being more floriferous and more resistant to diseases than "Fashion" and having a very good everblooming habit, with the foliage being larger, more glossy and less sharply serrate than that of "Spartan," attractive, high-centered buds that are more urn-shaped than those of "Spartan," a vigorous "floribunda" growing habit, with fewer thorns than the variety "Spartan," a habit of bearing the flowers mostly singly and on stems of good length, and a distinctive, attractive and remarkably uniform Shrimp Pink-Salmon general color tonality of the flowers somewhat similar to the flower color of "Spartan," but being more nearly Mandarin Red at the base of the inner surface of the flower petals and shading to Vermilion at the outer edges of the petals, with consequent less bi-color appearance than that of the flowers of "Spartan."

No references cited.